US005817082A

United States Patent [19]

Niedospial, Jr. et al.

[11] Patent Number: 5,817,082

[45] Date of Patent: Oct. 6, 1998

[54] MEDICAMENT CONTAINER CLOSURE WITH INTEGRAL SPIKE ACCESS MEANS

[75] Inventors: John J. Niedospial, Jr., Burlington, N.J.; Roger F. Hornick, Cary, Ill.; James M. Beck, Buffalo Grove, Ill.; Ricky Joel Law, Sr., Rockford, Ill.; John Sekowski, Long Grove, Ill.

[73] Assignee: Bracco Diagnostics Inc., Princeton, N.J.

[21] Appl. No.: 745,891

[22] Filed: Nov. 8, 1996

[51] Int. Cl.$^{6}$ .......................... A61B 19/00; B65D 41/20

[52] U.S. Cl. .......................... 604/414; 604/411; 215/247

[58] Field of Search .......................... 604/403, 404, 604/407, 411, 412, 414, 415, 416, 905; 215/247, 249, 250, 47, 48, 50

[56] References Cited

U.S. PATENT DOCUMENTS

| | | | |
|---|---|---|---|
| 2,289,677 | 7/1942 | Perelson | 215/47 |
| 2,326,490 | 8/1943 | Perelson | 215/47 |
| 2,342,215 | 2/1944 | Perelson | 215/38 |
| 2,667,986 | 2/1954 | Perelson | 215/48 |
| 3,872,992 | 3/1975 | Larson | 215/249 |
| 3,940,003 | 2/1976 | Larson | 215/247 |
| 3,977,555 | 8/1976 | Larson | 215/247 |
| 4,412,623 | 11/1983 | Schmidt | 215/11 |
| 4,568,346 | 2/1986 | Van Dijk | 604/414 |
| 4,982,769 | 1/1991 | Fournier et al. | 604/403 |
| 5,232,109 | 8/1993 | Tirrell et al. | 215/247 |
| 5,342,346 | 8/1994 | Honda et al. | 604/414 |
| 5,342,347 | 8/1994 | Kikuchi et al. | 604/403 |
| 5,354,287 | 10/1994 | Wacks | 604/403 |
| 5,364,386 | 11/1994 | Fukuoka et al. | 215/411 |
| 5,429,256 | 7/1995 | Kestenbaum | 215/247 |
| 5,433,330 | 7/1995 | Yatsko et al. | 215/247 |
| 5,533,994 | 7/1996 | Meyer | 604/403 |

*Primary Examiner*—John G. Weiss
*Assistant Examiner*—David J. Cho
*Attorney, Agent, or Firm*—Imre Balogh

[57] ABSTRACT

A disposable closure assembly/container combination for delivering medial fluid to a patient by needleless access means. The closure assembly comprises an elastomeric stopper for sealing the container at its open end and a spike access means equipped with a luer lock.

10 Claims, 4 Drawing Sheets

MEDICAMENT CONTAINER CLOSURE WITH INTEGRAL SPIKE ACCESS MEANS

BACKGROUND OF THE INVENTION

1. Field of the Invention

This invention relates to a closure used in conjunction with containers such as bottles, vials and bags containing pharmaceutical products for parenteral administration. More particularly, the invention relates to an elastomeric stopper for hermetically sealing a parenteral container, bottle, vial or bag the contents of which is accessed by the use of a spike integral with the stopper.

2. Reported Developments

Stopper systems for vials, bottles and the like are made of materials that are resistant to chemicals and pharmaceuticals such as corrosive materials, reagents, parenteral solutions and solid formulations reconstitutable with a solvent prior to use. The most commonly used stopper/vial system for such products has been glass or plastic bottles and vials equipped with rubber stoppers made of elastomeric materials. The system provides for good hermetical seal, safe storage and easy access to the content through the elastomeric stopper via the use of an infusion spike or a syringe when withdrawal of the content is desired. The elastomeric stopper used generally comprises an elastomeric base, such as natural or synthetic rubber and an inert coating covering at least some portions of the stopper. The coating used includes chlorobutyl rubber, polymeric fluorocarbon resins such as polytetrafluoroethylene and various thermoplastic films. The coating is intended to insulate the elastomeric stopper base from the contents of the container in order to prevent contact and possible chemical reactions therebetween.

Generally, the elastomeric stopper is of cylindrical shape and has a flange head portion overlying the open top end of the container. Integral with the head portion is a body portion which extends into the open end and seated in the neck portion of the container, the diameter of the body portion being somewhat larger than the inside diameter of the container so that a tight seal is created between the body portion and the wall of the container. The lower end of the body portion is beveled towards the central, longitudinal axis of the body portion to facilitate the insertion of the body portion into the container. The circular bottom surface that faces the contents of the container is substantially planar and is imperforate, having no recess therein. The head portion of the stopper is provided with a central recess extending downwardly from the top thereof a substantial distance into the body portion so that the central recess and the circular bottom surface define a diaphragm. The walls forming the recess are generally cylindrical but may be provided with one or more circular protuberances extending inwardly to terminate just short of the center line of the stopper. The circular protuberances serve to press against, seal and hold the needle of a syringe when the needle is inserted through the recess to penetrate the diaphragm for removal of the contents of the container. The elastomeric stopper is held in position by a metal ring or cap usually constructed of aluminum. The metal ring or cap has a removable center opening for allowing insertion of the syringe needle into the container.

Another type of the prior art stoppers has the needle penetrable diaphragm on the top portion of the stopper.

Various stopper and access systems exist in the prior art to hold and remove the contents of containers which are illustrated hereunder.

U.S. Pat Nos. 2,289,677 and 2,326,490 disclose a rubber stopper for use in vials comprising: an outer wall which serves a seal between the vial and the stopper; and an inner wall forming a chamber in the center of the stopper, the bottom portion of the inner wall serving as a diaphragm. A hollow needle, having a sharp end for piercing the diaphragm, and an outer end exposed for connection with a syringe, is carried by the outer wall. A syringe connected to the outer end of the needle and pushed inwardly effects piercing of the diaphragm thereby permitting aspiration of the contents of the vial.

U.S. Pat. No. 2,342,215 discloses a dispensing and sealing stopper for a vial comprising: a stopper body having a hollow needle therein, one end of said hollow needle is in constant communication with the contents of the vial, and the other end is sealed by a penetrable, thin membrane. When withdrawal of the contents of the vial is desired, a syringe is inserted into the stopper to penetrate the thin membrane and to engage the other end of the hollow needle. When the syringe is removed, the thin membrane self-closes to maintain the hollow needle and the contents of the vial sterile.

U.S. Pat. No. 5,232,109 discloses an elastomeric stopper for a bottle, said bottle includes an annular protuberance which forms a second seal with the shaft of a spike inserted in the stopper to prevent leakage, blow-out and introduction of particulate matter into the fluid-containing bottle.

U.S. Pat. No. 5,364,386 relates to an infusion unit which comprises: a flexible, large container, a small medicine vial and a pipe which serves to communicate between the large, flexible container and the small medicine vial.

The large container is adapted to hold a solvent or diluent, while the medicine vial contains a powdery medicine which is to be mixed and dissolved in the solvent or diluent contained in the large, flexible container. Upon dissolution, the mixed medicine is discharge through an outlet at the lower end of the large container for infusion into a patient.

U.S. Pat. No. 5,429,256 pertains to a drug withdrawal system for a vial. The withdrawal system comprises: a vial containing a medicament therein and closed with a rubber gasket; and an apparatus which snap fits on top of the vial. The apparatus comprises: a chassis and a cap which is attached to the cap by a living hinge.

The chassis is cylindrical and has vertical grooves on the external sides to facilitate handling. The top of the chassis has a central opening. The chassis includes a male luer lock adapter having external threads thereon, and a ferrule structure the lower end of which has a hollow sharpened lance. The apparatus is used with a syringe having a female luer lock connector which snap fits with the male luer lock adapter.

In use, a tamper evident tear seal on the cap cover is opened, and the outer cap is pressed toward the bottle contents. The lance penetrates the gasket on the vial thereby establishing flow communication with the contents in the vial. A syringe is then screwed onto the outer end of the adapter and then tightened on the adapter. The contents of the vial is withdrawn by pulling back on the plunger of the syringe. The syringe is then removed with the content therein ready to receive a needle assembly for injecting the contents into a patient.

U.S. Pat. No. 5,433,330 relates to a needleless access stopper used on containers with a cannula having a blunt stopper penetrating tip.

The present invention provides tamper evident sealing and access means for containers, such as bottles or vials made of glass or plastic, and bottles and bags made of plastic containing medical fluids, such as x-ray contrast media and parenteral liquids. For convenience the invention will be described in combination with containers. It is to be understood that the invention includes tamper evident sealing and access means for containers in general which comprise rigid or semi rigid access ports and capable of receiving such sealing and access means.

SUMMARY OF THE INVENTION

In accordance with the present invention, a closure assembly is provided for a container having a medical fluid therein, said closure assembly comprising:

an elastomeric stopper for hermetically sealing the container at its open end;

a spike access means to withdraw the contents of the container; and a tamper evident cover member for enclosing and sealing the spike access means onto the open end of the container and to maintain the spike access means and the elastomeric stopper free from contamination.

The elastomeric stopper is piercable and hermetically seals the medical fluid contained in the container. The elastomeric stopper has a head portion and a skirt portion integral with the head portion which comprises:

a) a flange extending laterally outwardly from the skirt portion and is designed to cover the transverse end surface of the neck of the container; and b) a target area at the center of the head portion designed to be pierced by the spike access means.

The elastomeric stopper used in the closure assembly of the present invention should be a fluid impervious, resilient, and inert without leachable additives therein in order to prevent any alteration of the product contained in the container. It may be of a single component or a blend of components. Examples of materials include synthetic or natural rubber, such as butyl rubber, isoprene rubber, silicone rubber, halogenated rubber, ethylene propylene therpolymer and the like. Specific examples of a synthetic elastomeric rubber include the $CH_2CF_2$—$C_3F_6(C_3F_5H)$ and the $C_2F_4$—$C_2F_3OCF_3$ series of elastomers made by DuPont under the trade names of VITON® and CARLEZ®; the fluoro-silicone rubbers, such as those made by Dow Corning under the trade name of SILASTIC®; and polyisobutylenes, such as VISTANEX MML-100 and MML-140; and halogenated butyl rubber, such as CHLOROBUTYL 1066, made by Exxon Chemical Company.

These or other suitable elastomers may be made into the desired stopper configuration by known methods. Such methods conventionally include the use of a curing agent, a stabilizer and a filler and comprise a primary and a secondary curing step at elevated temperatures.

The container used in conjunction with the present invention may be of glass or polymeric material, i.e., plastic, which are well known in the pharmaceutical industry. When the container is made of glass, it is in the shape of a vial or bottle. Polymeric materials are preferred for reasons of economy and safety. The plastic containers may be in the shape of a vial, bottle or bag. The vial or bottle is of rigid or semi-flexible polymeric material, while the bag is of a pliable polymeric material. In all shapes the container is provided with a neck portion which is rigid and retains its configuration so that it is capable of being hermetically sealed by the closure assembly of the present invention. The container comprises a neck portion having an interior surface, an interior radial surface, and a transverse end surface. The interior radial surface and the transverse end surface form the opening or mouth of the container. The neck portion further comprises an exterior surface which, being adjacent to the transverse end surface, forms an exterior radial ring. The exterior radial ring facilitates the holding of the closure assembly of the present invention. The container may have a volume capacity of from 5 ml to 5000 ml or more.

The mouth of the container is to receive the elastomeric stopper. The external diameter of the stopper is slightly larger than the internal diameter of the neck of the container so that on insertion of the stopper into the mouth of the container, a tight, hermetic seal is achieved.

After insertion of the stopper into the mouth of the container a cylindrical collar is positioned over the radial ring of the container and the stopper to securely hold the stopper in place. The cylindrical collar comprises: a flat top portion having a central opening therein so that the target, pierceable area of the stopper head remains exposed; a bottom portion; and a cylindrical side portion having an inner wall and an outer wall. The inner wall incorporates an inwardly projecting ring which, upon assembly, is positioned below the exterior radial ring of the neck portion of the container so as to securely hold the elastomeric stopper in the container. The outer wall of the cylindrical side portion of the cylindrical collar incorporates an annular groove and, spaced from the annular groove, an annular protuberance at the bottom portion of the cylindrical collar projecting outwardly. The annular groove is to receive the spike access means when the spike access means is in its stationary or inactivated position, and the annular protuberance serves as a stop means to the spike access means after its activation. The cylindrical collar may be made of rigid polymeric material so that it retains its configuration or metal such as aluminum.

The spike access means has an inverted, essentially U-shape configuration having a top portion, side portion and a bottom portion. The top portion at its center incorporates a spike which comprises: a cylindrical shaft having a channel therein terminating in a sharp tip at one end thereof; and a male or female luer connector at the other end thereof to engage a corresponding female or male luer lock at the end of an IV tubing which delivers the medical fluid into a patient. The bottom portion of the spike access means incorporates an annular protuberance projecting inwardly towards the container, which fits into the annular groove of the cylindrical collar. The spike access means is positioned over the annular cylindrical collar by fitting the annular protuberance into the annular groove. In this initial position, the spike access means is in an inactivated stage because the sharp tip of the spike is just very slightly above the center, pierceable target area of the elastomeric stopper.

The spike access means is made of a rigid but slightly flexible polymeric material so that, when activation of the same is desired, the sides of the annular collar flex outwardly as a result of manual force exerted on the top portion of the spike access means. The exerted manual force will dislodge the annular protuberance from the annular groove and slides the spike access means downward so that the sharp tip of the spike penetrates the center target area of the elastomeric stopper thereby providing access to the medical fluid contained in the container. The spike access means, in its sliding downward motion, will be stopped when the annular protuberance of the spike access means reaches the annular protuberance on the bottom of the cylindrical collar.

A removable cover member completely encloses the spike access means along with the elastomeric stopper and the neck portion of the container. The removable cover is made of plastic, or metal such as aluminum. The removable cover at its bottom portion is sealed to the neck of the container by a tear strip. At the point of use, the tear strip is removed. This allows the removable cover member to be pushed axially toward the container. During the axial movement the spike penetrates the target area thereby establishing fluid communication with the contents of the container. Upon activation the removable cover member is removed revealing the female luer connector with locking threads thereon. A male luer connector is then attached and the contents is either delivered to the patient via a tubing and catheter, direct injection for therapeutic drugs, or transferred to another container for subsequent administration to the patient.

BRIEF DESCRIPTION OF THE DRAWINGS

With reference to the annexed drawings, illustrating the invention.

DESCRIPTION OF THE PREFERRED EMBODIMENT

Figure 5:
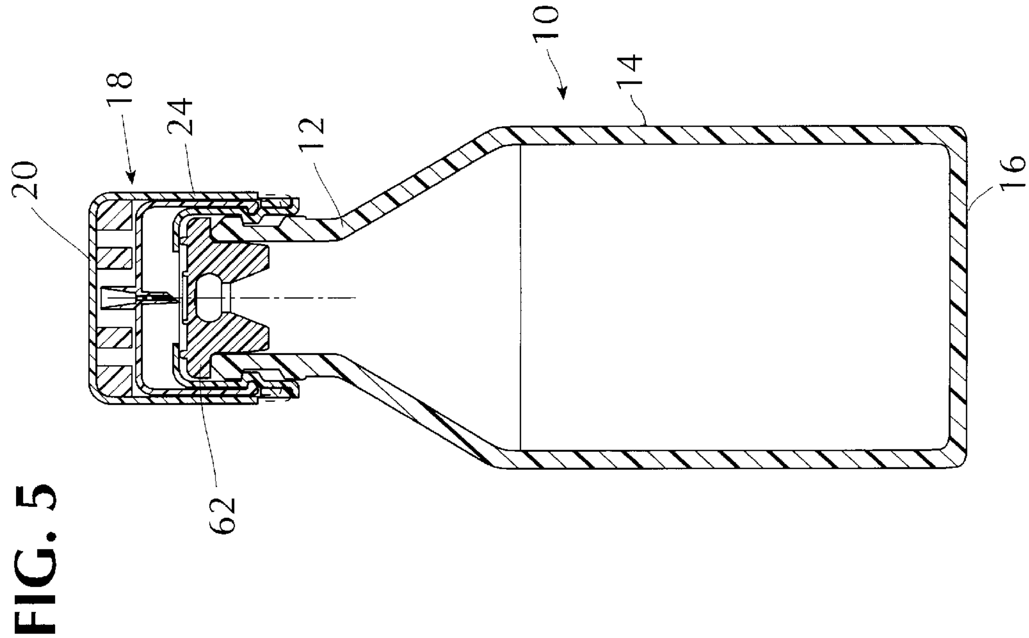
FIG. 5 is a section al view of the container, the stopper with the spike access means and the removable cover member taken along the line 4—4 of FIG. 1.

Referring to FIGS. 1, 2, 4, 5 and 7, the container 10 having an open end in which the closure assembly of the present invention is used comprises a neck portion 12, a side portion 14, and a bottom portion 16. The closure assembly is covered with a cylindrical removable cover member 18 having a flat top portion 20, a bottom portion 22 which is sealed to the neck portion 12 of the container 10 by a tear strip 25 and side portion 24.

Located on the underside of the removable cover member 18 are two or more equally spaced ribs 19 which are provided to allow the removable cover member to withstand the forces associated with capping and stacking during sterilization. The ribs serve to transfer any external force directly to the spike access means without coming in contact with the luer connector 118.

Figure 6:
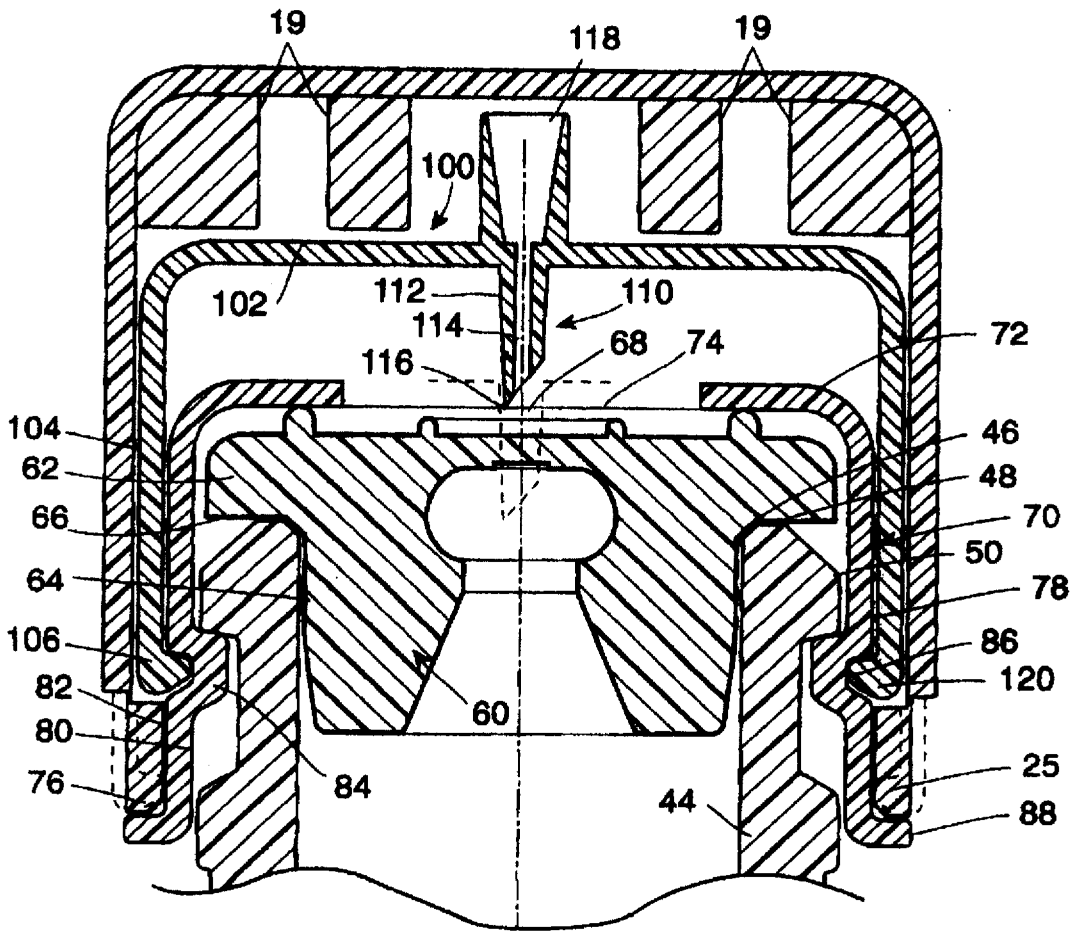
FIG. 6 is a sectional view of the neck portion of the container, the stopper with the spike access means and the removable cover member shown in FIG. 1.
Figure 8:
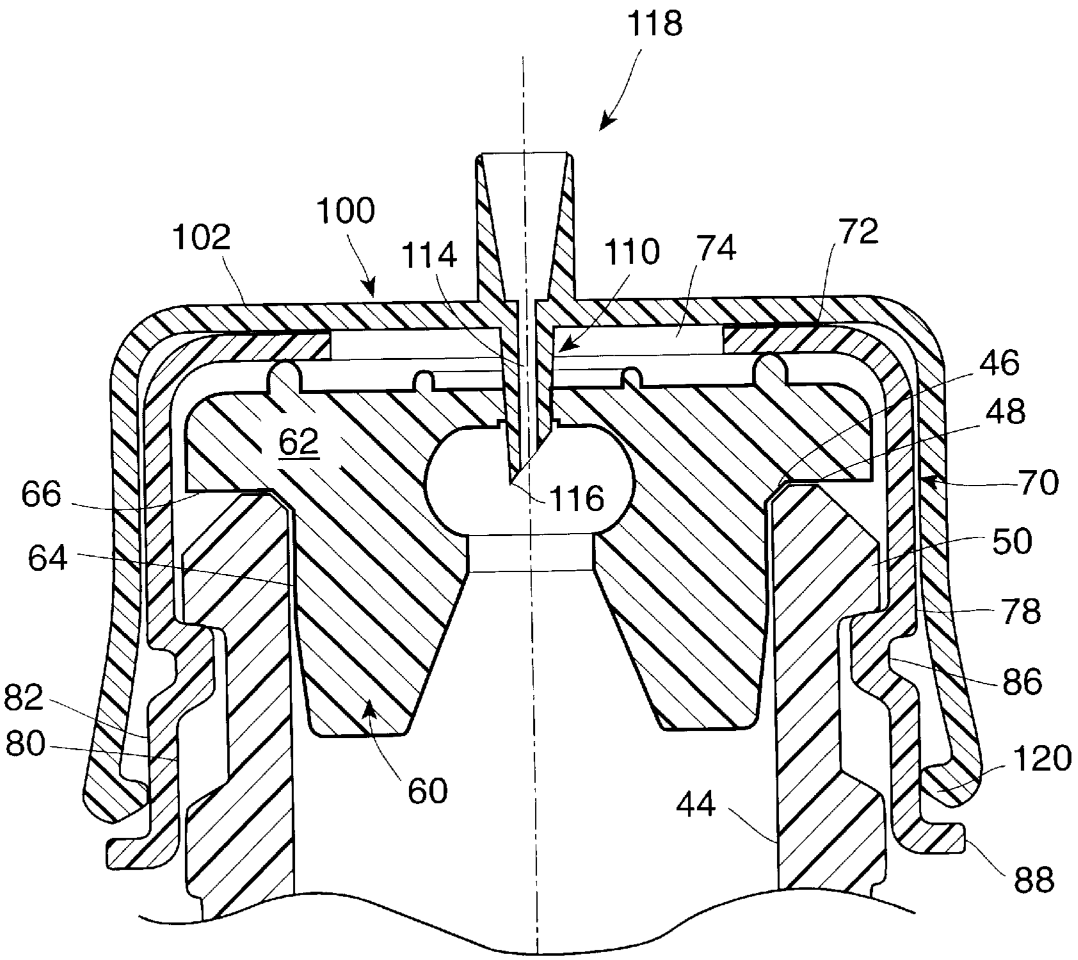
FIG. 8 is a sectional view of the neck portion of the container, and the stopper with the spike access means having penetrated the target area in the stopper.

Referring to FIGS. 5, 6 and 8, the container 10 comprises a neck portion 12 having an interior surface 44, and interior radial end surface 46 on the top end portion of the interior surface 44, and transverse end surface 48. The interior radial surface and the transverse end surface form the mouth of container 10. The neck portion 12 further comprises an exterior surface which, adjacent to the transverse end surface 48, evolves into an exterior radial ring 50. The exterior radial ring is adapted to facilitate the holding of the closure assembly, described later.

The mouth of the container is to receive an elastomeric stopper 60, as shown in FIGS. 5, 6 and 8. The elastomeric stopper 60 comprises a head 62 and integral therewith a skirt 64. The head 62 comprises: a flange 66 extending laterally outwardly from skirt 64 and is adapted to cover transverse end surface 48 of container 10; and a target area 68 which is adapted to be pierced by a spike access means.

As best seen in FIGS. 6 and 8 the container 10, after being filled with the desired amount of medical fluid, is sealed with the elastomeric stopper 60. To hold the elastomeric stopper securely in place and to serve as a receiving means for the spike access means, a cylindrical collar 70 is fastened over a portion of the elastomeric stopper 60 and the neck 12 of the container 10. The cylindrical collar 70 comprises:

a flat top portion 72 having a central opening therein 74 so that the target area 68 in the elastomeric stopper 60 remains exposed;

a circular bottom portion 76; and a cylindrical side portion 78 having an inner wall 80 and an outer wall 82.

The inner wall 80 incorporates an inwardly projecting ring 84 which is positioned below the exterior radial ring 50 of the neck portion 12 of container in order to securely hold the elastomeric stopper 60 in container 10.

The outer wall 82 of cylindrical side portion 78 of cylindrical collar 70 incorporates: an annular groove 86; and an annular protuberance 88 projecting outwardly at the bottom portion of the cylindrical collar 70. The annular groove 86 is to receive the spike access means when the spike access means is in its stationary or inactivated position, while the annular protuberance 88 serves as a stop means after the activation of the spike access means.

The spike access means 100 has an inverted U-shaped configuration in sectional view having: a top portion 102; a side portion 104; and a bottom portion 106. The top portion 102 at its center incorporates a spike 110 which comprises: a cylindrical shaft 112, having a channel therein 114, terminating in a sharp tip 116 at the lower end thereof; and a female Luer connector 118 at the other end thereof to engage a corresponding male Luer connector at the end of an IV tubing (not shown)which delivers the medical fluid contained in the container into a patient.

The bottom portion 106 of spike access means 100 incorporates an annular protuberance 120 projecting inwardly towards the container and engages the annular groove 86 of cylindrical collar 70. During assembly the spike access means 100 is positioned over the annular cylindrical collar 70 by fitting the annular protuberance 120 of the spike access means 100 into the annular groove of the cylindrical collar 86. As shown in FIG. 6, in this initial position the spike access means is in an inactivated stage because the sharp tip of the spike does not penetrate the target area of the elastomeric stopper. However, it may be preferred to allow the spike to contact, but not penetrate, the stopper to minimize the required stroke/range of axial movement to accomplish reliable penetration of the stopper. The container 10, having the medical fluid therein, is capped with removable cover member 18 and the removable cover member is sealed to the neck of the container with a tear strip 25. The container is then sterilized, shipped and stored ready to be used.

Figure 1:
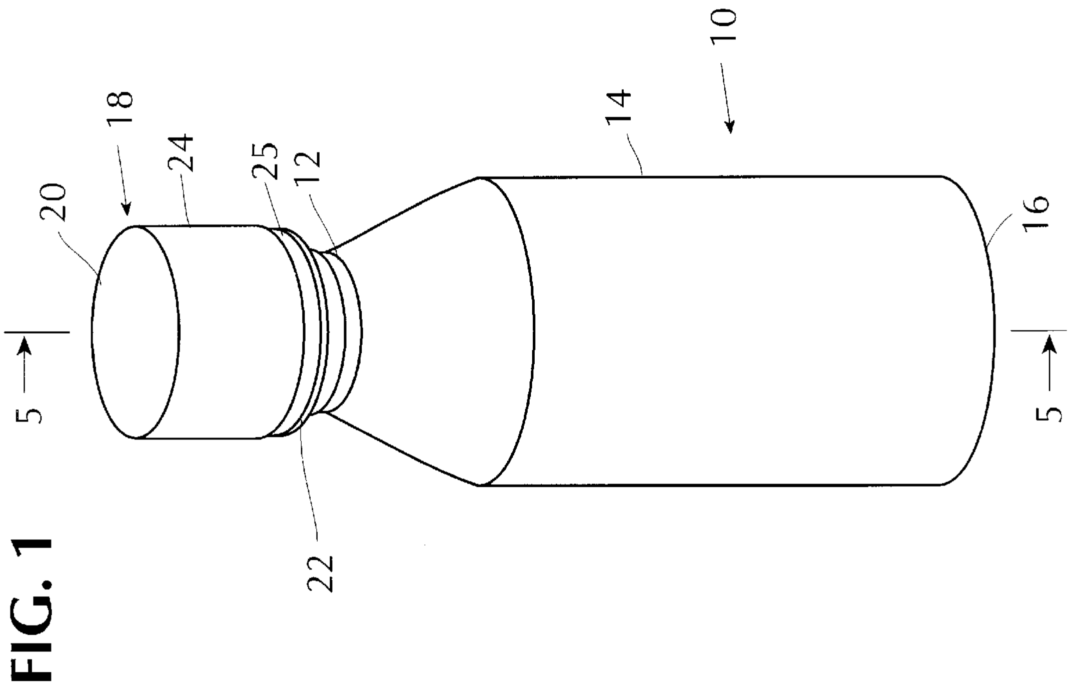
FIG. 1 is a perspective view of a container, a stopper with spike access means, and removable cover member.
Figure 2:
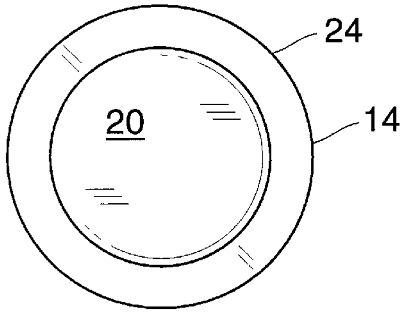
FIG. 2 is a top plan view thereof.
Figure 3:
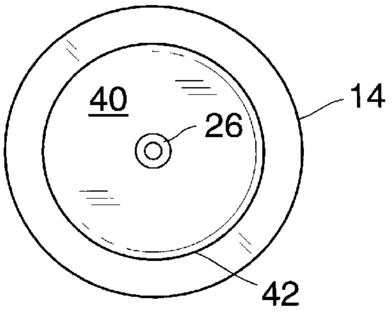
FIG. 3 is a top plan view thereof without the removable cover member.
Figure 4:
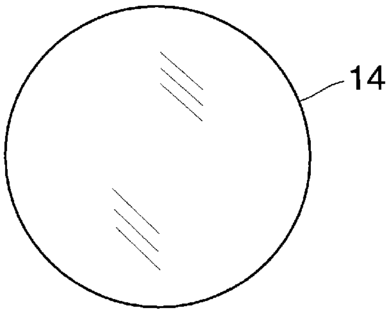
FIG. 4 is a bottom plan view thereof.
Figure 7:
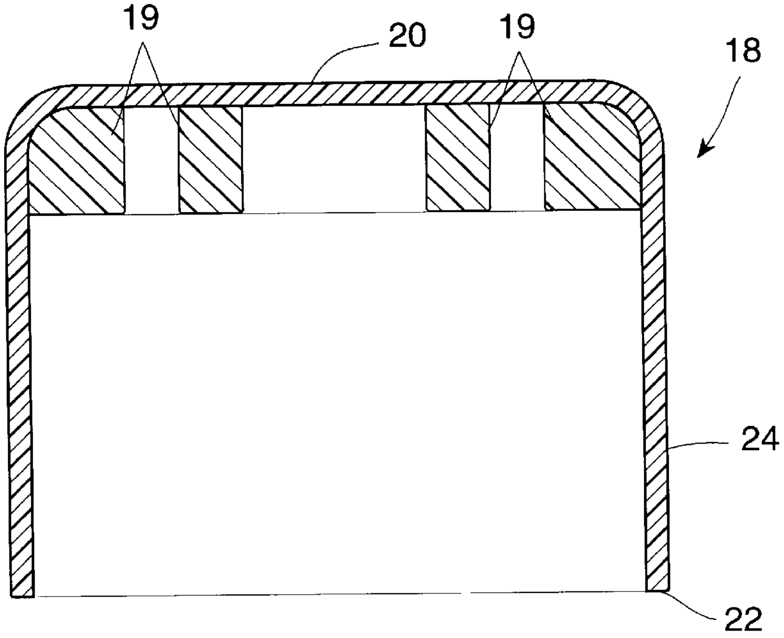
FIG. 7 is a sectional view of the removable cover member removed form the container shown in FIG. 1.

The removable cover member 18 as shown in FIG. 7 completely encloses the spike access means 100 and the neck portion 12 of the container 10 as shown in FIGS. 1, 5 and 6.

When it is desired to deliver medical fluid to a patient, the tear strip 25 is removed and manual force is exerted onto the removavle cover member 18. The force so exerted dislodges annular protuberance 120 on spike access means 100 from annular groove 86 of cylindrical collar 70. As the exertion of force continues, the side portion 104 of spike access means 100 flexes outwardly from the container. At the same time the sharp tip 116 of shaft 112 of spike 110 penetrates the target area 68 of the elastomeric stopper 60. Spike access means 100 ti-avels downward into the container until annular protuberance 120 on the spike access means reaches protuberance 88 of the cylindrical collar 70. At this point, the top portion 102 of the spike access means 100 also reaches the flat top portion 72 of the cylindrical collar 70. The removable cover member 18 is then removed exposing the underlying female luer connector 118 to which an IV line, having a male luer connector, is attached. The medical fluid in the container is ready for delivery to the patients by turning the container upside-down.

The present invention has been described in connection with the preferred embodiment shown in the drawings, however, various changes and modifications will be apparent to those skilled in the art.

| PARTS LIST | |
|---|---|
| Container | 10 |
| Neck portion of container | 12 |
| Side portion of container | 14 |
| Bottom portion of container | 16 |
| Cylindrical removable cover member (of closure assembly) | 18 |
| Ribs on cylindrical removable cover member | 19 |
| Flat top portion of removable cover member | 20 |
| Bottom rim portion of removable cover member | 22 |
| Cylindrical side portion of removable cover member | 24 |
| Tear strip on the base of the removable cover member | 25 |
| Interior surface of the neck portion of container | 44 |
| Interior radical end surface of the neck portion of container | 46 |
| Transverse end surface of container | 48 |
| Exterior radial ring of neck portion of container | 50 |
| Elastomeric stopper | 60 |
| Head of elastomeric stopper | 62 |
| Skirt of elastomeric stopper | 64 |
| Flange of head of elastomeric stopper | 66 |
| Target area of elastomeric stopper | 68 |
| Cylindrical collar | 70 |
| Flattop portion of cylindrical collar | 72 |
| Central opening in the flat top portion of the cylindrical collar | 74 |
| Circular bottom portion of cylindrical collar | 76 |
| Cylindrical side portion of cylindrical collar | 78 |
| Inner wall of cylindrical side portion | 80 |
| Outer wall of cylindrical side portion | 82 |
| Inwardly projecting ring of inner wall | 84 |
| Annular groove of cylindrical collar | 86 |
| Annular protuberance of cylindrical collar | 88 |
| Spike access means | 100 |
| Top portion of spike access means | 102 |
| Side portion of spike access means | 104 |
| Bottom portion of spike access means | 106 |
| Spike | 110 |
| Cylindrical shaft of spike | 112 |
| Channel in shaft | 114 |
| Sharp tip of shaft | 116 |
| luer Connector | 118 |
| Annular protuberance on spike access means | 120 |

What is claimed is:

1. A disposable closure assembly/container combination, said container having a medical fluid therein, said closure assembly having a needleless access means allowing withdrawal of said medical fluid from said container by use of an intravenous tubing attached to said needleless access means, said disposable closure/container combination comprising:

a) a container, containing a medical fluid therein, which comprises:

a1) a neck portion having an interior radial surface and a transverse end surface forming the mouth of said container;

a2) an exterior surface which, with said transverse end surface, forming a radial ring to receive and hold a cylindrical collar;

b) a closure assembly consisting of an elastomeric stopper, a cylindrical collar and a spike access means, said elastomeric stopper comprising:

b1) a head portion and a skirt portion, said head portion having: a flange extending laterally outwardly form said skirt portion and is designed to cover the mouth of the container; and a target area at the center of the head portion designed to be pierced by a spike access means; and said skirt portion projecting into the container sealing the medical fluid contained therein;

b2) said cylindrical collar comprising: a flat top portion having a central opening therein superimposed on the target area in the head portion of the elastomeric stopper; a cylindrical side portion having an inner wall, an outer wall, and a bottom portion; said inner wall having an inwardly projecting ring positioned below the exterior radial ring on the container to securely hold the elastomeric stopper in the container; said outer wall of said cylindrical side portion having: an annular groove to receive and engage a spike access means; and an annular protuberance at the bottom portion of said cylindrical collar projecting outwardly to serve as stopping means for said spike access means;

b3) said spike access means positioned over and enveloping said cylindrical collar, said spike access means comprising: a top portion; a side portion; and a bottom portion;

b4) said top portion having an integral spike at the center thereof which comprises a cylindrical shaft having a fluid communicating channel therein and terminating in a sharp tip at one end thereof for piercing the target area in said elastomeric stopper, and a female luer lock at the other end thereof to engage a corresponding male luer lock contained at the end of a fluid delivery tubing;

b5) said side portion overlaps the outer wall of said cylindrical collar and is slidable thereon;

b6) said bottom portion having an annular protuberance thereon projecting inwardly towards the container and engaging the annular groove in said cylindrical collar thereby providing an initial pre-piercing position for said spike access means; said spike access means being capable of axial, slidable movement so that upon vertical pressure said inwardly projecting protuberance is being dislodged from said annular groove and said sharp tip of said cylindrical shaft penetrates said target area in the elastomeric stopper thereby providing access to the medical fluid contained in he container; and c) a removable cover member enclosing the spike access means onto the neck of the container to maintain the closure assembly free from contamination.

2. The disposable closure assembly/container combination of claim 1 wherein said container is made of glass.

3. The disposable closure assembly/container combination of claim 1 wherein said container is made of a polymeric material.

4. The disposable closure assembly/container combination of claim 1 wherein said container is made of a flexible or pliable polymeric material.

5. The disposable closure assembly/container combination of claim 1 wherein said container is a vial.

6. The disposable closure assembly/container combination of claim 1 wherein said container is a bottle.

7. The disposable closure assembly/container combination of claim 1 wherein said container is a pouch or bag.

8. The disposable closure assembly/container combination of claim 1 wherein said medical fluid contained in said container is an x-ray contrast medium.

9. The disposable closure assembly/container combination of claim 1 wherein said medical fluid contained in said container is a parenteral liquid.

10. The disposable closure assembly/container combination of claim 1 wherein said container contains of from about 5 ml to about 5000 ml of said medical fluid therein.

* * * * *